US009114011B2

(12) United States Patent
Lee et al.

(10) Patent No.: US 9,114,011 B2
(45) Date of Patent: Aug. 25, 2015

(54) FABRICATION METHOD OF A NOVEL ARTIFICIAL CORTICAL BONE USING A MULTI-PASS EXTRUSION PROCESS

(75) Inventors: Byong Taek Lee, Cheonan-si (KR); Dong Woo Jang, Cheonansi (KR)

(73) Assignee: SOONCHUNHYANG UNIVERSITY INDUSTRY ACADEMY COOPERATION FOUNDATION, Chungcheongnam-Do (KR)

( * ) Notice: Subject to any disclaimer, the term of this patent is extended or adjusted under 35 U.S.C. 154(b) by 281 days.

(21) Appl. No.: 13/700,846

(22) PCT Filed: Jul. 26, 2011

(86) PCT No.: PCT/KR2011/005509
§ 371 (c)(1),
(2), (4) Date: Nov. 29, 2012

(87) PCT Pub. No.: WO2012/015226
PCT Pub. Date: Feb. 2, 2012

(65) Prior Publication Data
US 2013/0085578 A1    Apr. 4, 2013

(30) Foreign Application Priority Data
Jul. 27, 2010   (KR) .................. 10-2010-0072191

(51) Int. Cl.
*C04B 35/447*  (2006.01)
*A61F 2/28*  (2006.01)
*A61L 27/42*  (2006.01)

(52) U.S. Cl.
CPC ............... *A61F 2/28* (2013.01); *A61L 27/425* (2013.01); *C04B 35/447* (2013.01); *A61L 2430/02* (2013.01)

(58) Field of Classification Search
CPC ................ C04B 35/447; C04B 2235/3212; B28B 3/2636
USPC ........................................................ 264/638
See application file for complete search history.

(56) References Cited

U.S. PATENT DOCUMENTS
2007/0255422 A1   11/2007   Wei et al.

FOREIGN PATENT DOCUMENTS

| JP | 2006-006756 | 1/2006 |
| JP | 2009-535101 | 10/2009 |
| KR | 10-2005-0020578 | 3/2005 |

OTHER PUBLICATIONS

Machine Translation of JP 2006-006756.*
Translation of JP 2006-006756.*
International search report dated Mar. 13, 2012 in corresponding PCT/KR2011/005509.

* cited by examiner

*Primary Examiner* — Joseph S Del Sole
*Assistant Examiner* — Russell Kemmerle, III
(74) *Attorney, Agent, or Firm* — Revolution IP, PLLC

(57) ABSTRACT

A method for fabricating an artificial bone by multi-pass extrusion, includes: a first extrusion process of forming roll-shaped filaments having sheets of calcium phosphate/calcium phosphate-(t-$ZrO_2$)/t-$ZrO_2$; a second extrusion process of arranging the prepared roll-shaped filaments circularly and extruding the same; and a third extrusion process of forming an external shell of hydroxyapatite (HAp). The method for fabricating an artificial bone allows fabrication of an artificial bone having the biocompatibility and mechanical strength of the natural bone and may be utilized variously in biomedical engineering, medicine and other applications.

6 Claims, 4 Drawing Sheets

FABRICATION METHOD OF A NOVEL ARTIFICIAL CORTICAL BONE USING A MULTI-PASS EXTRUSION PROCESS

TECHNICAL FIELD

The present disclosure relates to a method for fabricating an artificial bone using a multi-pass extrusion process and an artificial bone fabricated by the method.

BACKGROUND ART

Bone grafting performed by orthopedic surgeons to repair bone fractures can be largely classified into autograft, allograft and artificial bone graft. Among them, autograft shows excellent biocompatibility, but it is disadvantageous in that the size of bone is limited and the bone has to be harvested from the patient's own body. Allograft is associated with the problem that the bone is often obtained from a cadaver of an unknown source. Also, the donated bone may cause infections. Thus, development of an artificial bone capable of replacing the natural bone is strongly required. However, there remain problems with regard to improvement in biocompatibility with the human body and mechanical strength.

The natural bone exhibits better strength than any other synthetic materials developed for artificial bone thus far. This may be due to the characteristic lamellar microstructure of the natural bone. The most important factor in developing artificial bone is to provide superior mechanical property as well as biocompatibility.

Although many researchers are striving to mimic the natural bone using bioceramics, an artificial bone satisfying both biocompatibility and mechanical strength is not developed as yet.

DISCLOSURE

Technical Problem

Specifically, the present disclosure is directed to providing a method for fabricating an artificial bone satisfying both biocompatibility and mechanical strength based on a multi-pass extrusion process-based shape control technique.

Technical Solution

In one general aspect, the present disclosure provides a method for fabricating an artificial bone by multi-pass extrusion, including: a first extrusion process of forming roll-shaped filaments comprising sheets of calcium phosphate/calcium phosphate-(t-$ZrO_2$)/t-$ZrO_2$; a second extrusion process of arranging the prepared roll-shaped filaments circularly and extruding the same; and a third extrusion process of forming an external shell of hydroxyapatite (HAp).

In an embodiment, the calcium phosphate may be hydroxyapatite (HAp) or tricalcium phosphate (TCP), although not limited thereto. The calcium phosphate-based ceramics such as hydroxyapatite (HAp) or tricalcium phosphate (TCP) have superior biocompatibility because they are similar to the natural bone.

t-$ZrO_2$ is bioinert and has superior mechanical strength. However, it may degrade biocompatibility and, when implanted in the body, may be not fully biodegradable and lead to incomplete ossification at the implanted site. In the present disclosure, a lamellar structure of three layers including calcium phosphate and t-$ZrO_2$ is formed to provide superior biocompatibility and mechanical strength.

For example, in the first extrusion process, shells of a three-layered lamellar structure of HAp/HAp-(t-$ZrO_2$)/t-$ZrO_2$ or TCP/TCP-(t-$ZrO_2$)/t-$ZrO_2$ are extruded. And, extrusion is performed using an extrusion mold with the same diameter in order to obtain carbon filaments with the same diameter.

The filaments obtained from the first extrusion process are aligned in a mold and subjected to second extrusion. In the second extrusion process, the carbon filaments are aligned at the center and the roll-shaped filaments are arranged to surround the carbon filaments. The number of the filaments may be adjusted for thickness control.

Then, third extrusion is performed after preparing a shell of HAp and arranging it to surround the extruded filaments.

In an embodiment, the method for fabricating an artificial bone may include a burning out process and a sintering process after the third extrusion process. More specifically, the method for fabricating an artificial bone may include, after the third extrusion process, a first burning out process at 600-800° C.; a second burning out process at 900-1100° C.; and a sintering process at 1400-1600° C. Additive components such as EVA are removed through the first burning out process, and the carbon components are removed through the second burning out process to form pore channels. Physical properties of the fabricated artificial bone may be different depending on the temperature in the sintering process. The temperature of the sintering process may be 1400-1600° C., more specifically 1500° C.

In another general aspect, the present disclosure provides an artificial bone fabricated by the above-described method. Other features and aspects will be apparent from the following detailed description, the drawings, and the claims.

Advantageous Effects

The method for fabricating an artificial bone according to the present disclosure allows fabrication of an artificial bone having the biocompatibility and mechanical strength of the natural bone and may be utilized variously in biomedical engineering, medicine and other applications.

DESCRIPTION OF DRAWINGS

The above and other objects, features and advantages of the present disclosure will become apparent from the following description of certain exemplary embodiments given in conjunction with the accompanying drawings, in which.

BEST MODE

Hereinafter, the embodiments of the present disclosure will be described in detail with reference to accompanying drawings.

Example 1

Figure 1:
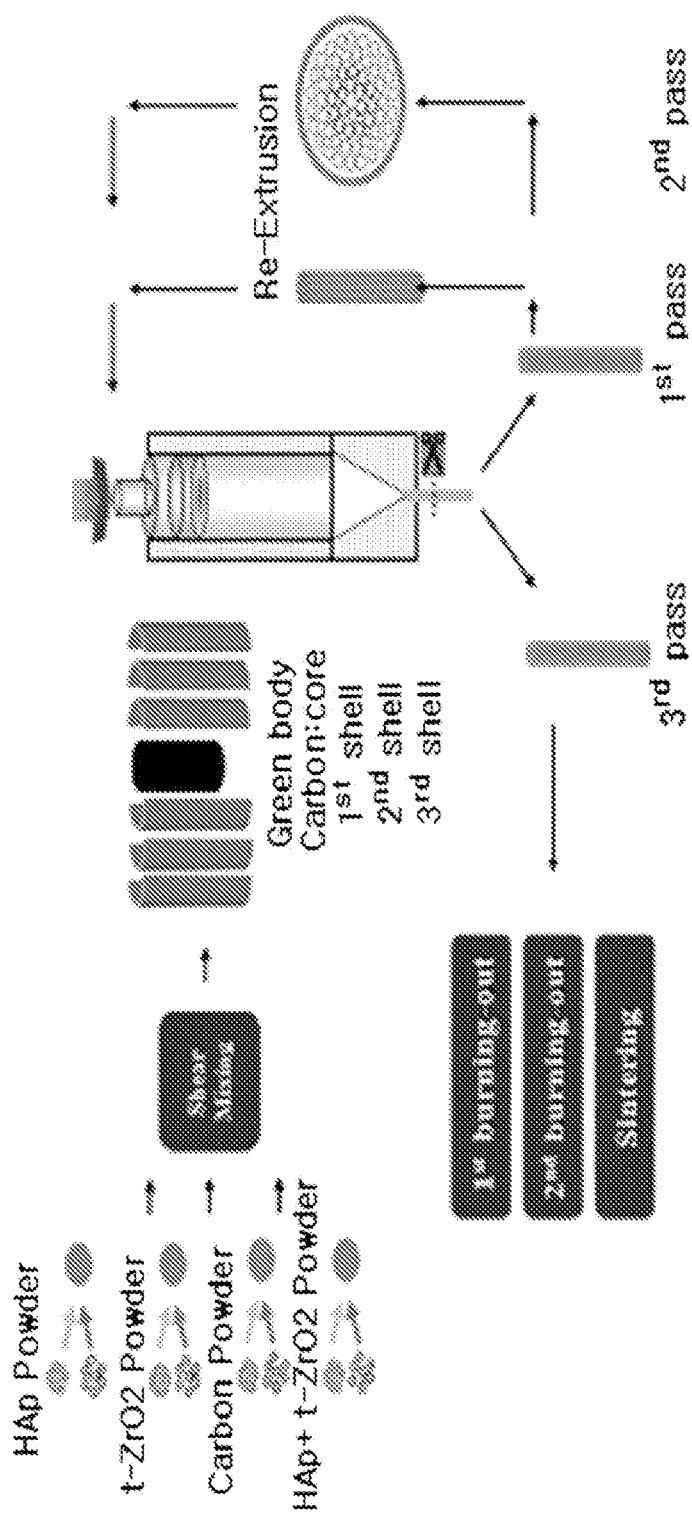
FIG. 1 schematically shows a process of fabricating an artificial bone according to an embodiment of the present disclosure.

An artificial bone suitable to be used as a finger bone was fabricated. FIG. 1 schematically shows the fabrication process. HAp (ca. 100 nm, microwave-assisted process) and t-$ZrO_2$ (ca. 70 nm, TZ-3Y, Tosoh, Japan) were used as powder source. Carbon powder (15 μm, Aldrich, USA) was used to form a porous structure, and ethylene vinyl acetate (EVA; ELVAX 210 and 250, DuPont, USA) and stearic acid (Daejung Chemicals & Metals Co. Korea) were used as binder and lubricant, respectively.

HAp (HAp 48 vol %/EVA 42 vol %/stearic acid 10 vol %), carbon (carbon 48 vol %/EVA 42 vol %/stearic acid 10 vol %) and t-$ZrO_2$ (t-$ZrO_2$ 43 vol %/EVA 45 vol %/stearic acid 12 vol %) composites were synthesized using a shear mixer (Shina Platec, Korea).

HAp, HAp-(t-$ZrO_2$) and t-$ZrO_2$ shells were prepared by warm pressing. Extrusion was performed after surrounding the carbon composite with the shells. The shells were arranged in the order of HAp, HAp-(t-$ZrO_2$) and t-$ZrO_2$ from inside. Extrusion was performed using an extrusion mold with the same diameter in order to obtain carbon filaments with the same diameter. Sixty-one (61) filaments of diameter 3.5 mm obtained from the first extrusion process were arranged in the same mold and subjected to second extrusion. The arrangement of the filaments was controlled to allow the role of a finger bone. A plurality of the carbon filaments of diameter 3.5 mm were arranged inside to ensure a space for the spongy bone during burning out. Then, the filaments of osteon structure resulting from the second extrusion were arranged so as to form the compact bone layer. The number of the filaments may be adjusted for thickness control. Next, third extrusion was performed after surrounding with an HAp shell prepared by warm pressing.

In order to remove the binder, ethylene vinyl acetate (EVA), first burning out was performed while gradually changing temperature to 700° C. under nitrogen atmosphere. In order to remove the carbon used to form the porous structure, second burning out was performed while gradually changing temperature to 1000° C. under air atmosphere. Finally, sintering was performed using microwaves for 10 minutes at 1500° C.

Figure 2:
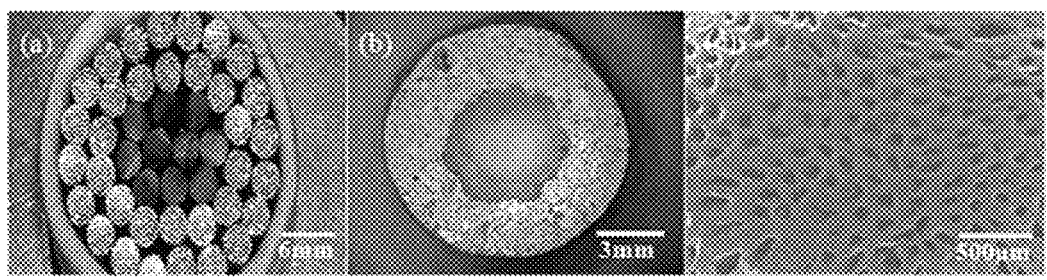
FIG. 2 shows a cross-sectional view of filaments arranged in a mold prior to third extrusion (a), a cross-sectional view of an artificial bone after sintering (b), and a partial enlarged view thereof (c)

FIG. 2 shows a cross-sectional view of the filaments arranged in the mold prior to the third extrusion (a), a cross-sectional view of the artificial finger bone after the sintering (b), and its partial enlarged view (c).

First, referring to FIG. 2, (a), the 34 filaments arranged in two layers serve to form Haversian canals. The black portion is the carbon components and the external shell is made of HAp to improve biocompatibility. FIG. 2, (b) shows the artificial finger bone obtained from the third extrusion at 1500° C. The void in the center portion is the region for the spongy bone where bone marrow is contained. FIG. 2, (c) is an enlarged SEM of the compact bone portion of FIG. 2, (b). It can be seen that carbon was removed and holes were formed instead through the burning out process. The individual filaments were attached well with no cracking or splitting and pore channels formed as the carbon was removed were distributed well.

Figure 3:
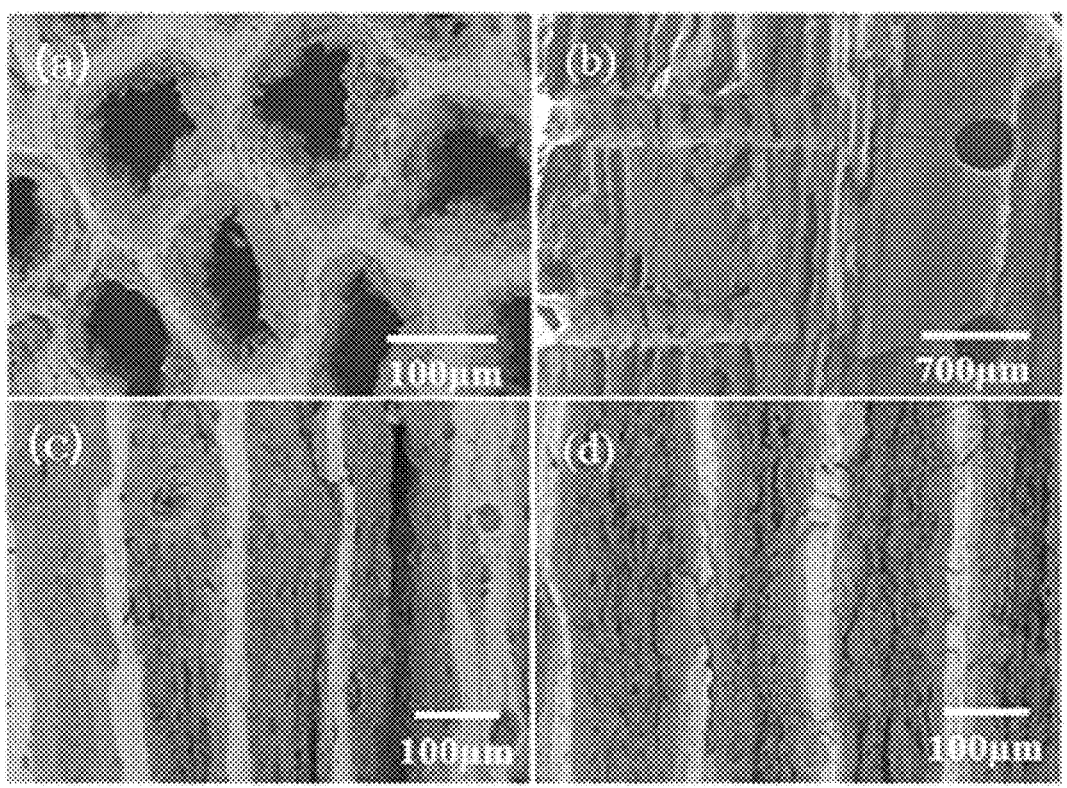
FIG. 3 shows cross-sectional SEM images of an artificial bone after first burning out (a), after second burning out (b), and after sintering at 1500° C. (c) or at 1350° C. (d)

FIG. 3 shows cross-sectional SEM images of the artificial bone after the first burning out (a), after the second burning out (b), and after the sintering at 1500° C. (c) or at 1350° C. (d).

Referring to FIG. 3, (a), the ethylene vinyl acetate (EVA) used as the binder was removed in the first burning out process at 700° C. And, referring to FIG. 3, (b), the carbon components were removed in the second burning out, which was performed under air atmosphere at 1000° C., to form pore channels. The pores have a diameter of about 86.1 μm, and the frame thickness between the pores is about 57 μm. The pores will serve like the Haversian canals of the natural bone. FIG. 3, (b) shows linear pores which will serve as Volkmann's canals. Volkmann's canals play an important role of connection with the Haversian canals and transport of blood and other materials. The Volkmann's canals were formed mechanically using a 500 μm drill. After the sintering, the canals were contracted to a diameter of about 377 μm.

FIGS. 3, (c) and (d) respectively show the longitudinal cross-section of the microstructure of the artificial bone after the sintering at 1500° C. and 1350° C. The TCP/TCP-(t-$ZrO_2$)/t-$ZrO_2$ filaments arranged well continuously in one direction are clearly seen. The bright portion comprises t-$ZrO_2$ and the dark portion comprises TCP. The fine cracks and pores seen in FIG. 3, (d) are caused by the difference in the coefficients of thermal expansion of TCP and t-$ZrO_2$ at 1350° C. The microstructure was much less fine when the sintering was performed at 1350° C. as compared to when the sintering was performed at 1500° C. because t-$ZrO_2$ requires high temperature for sintering.

Figure 4:
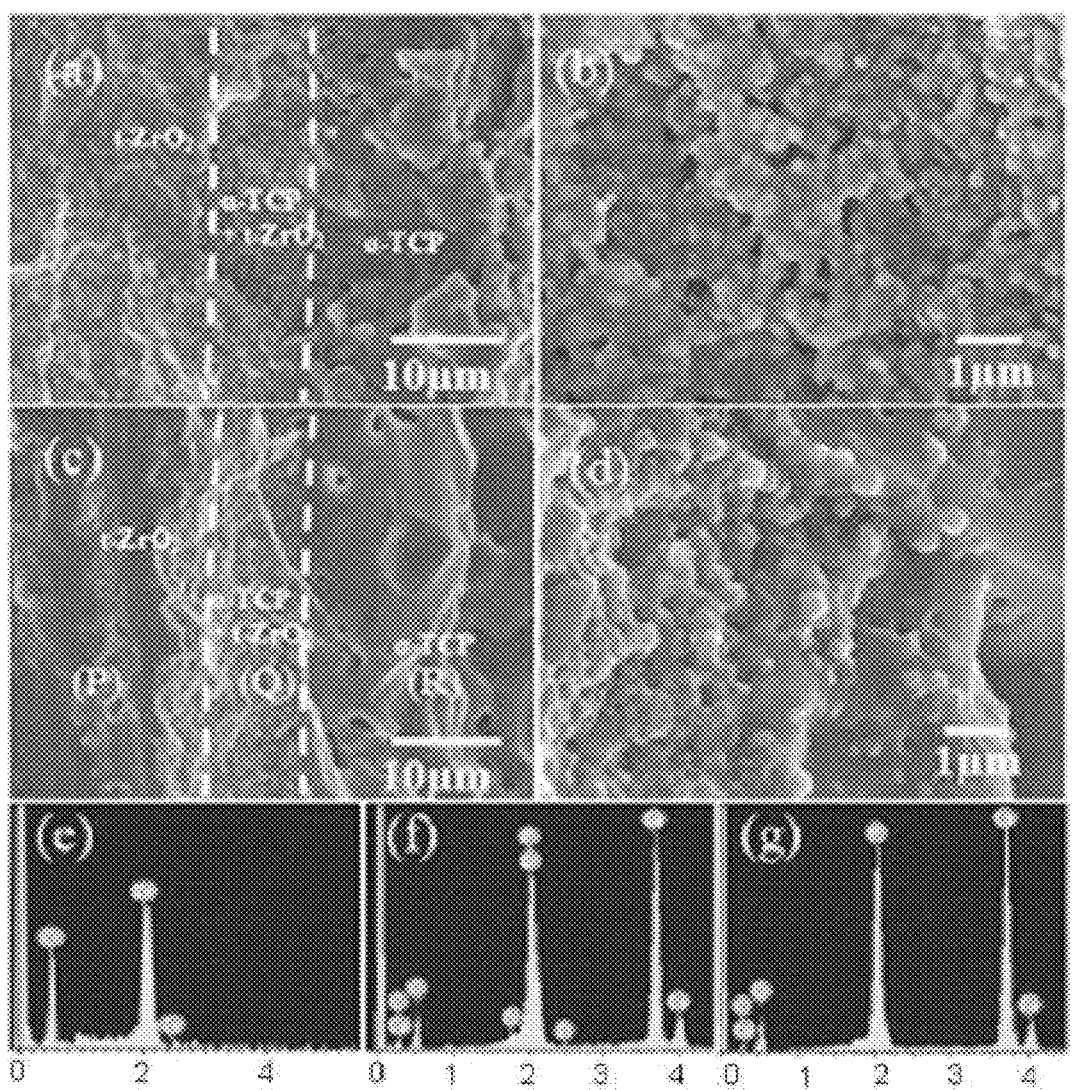
FIG. 4 shows cross-sectional SEM images of a TCP/TCP-(t-$ZrO_2$)/t-$ZrO_2$ composite.

FIG. 4 shows cross-sectional SEM images of the TCP/TCP-(t-$ZrO_2$)/t-$ZrO_2$ composite. The composite was composed of TCP, TCP-(t-$ZrO_2$) and t-$ZrO_2$ regions. The respective layers are clearly divided by the broken lines shown in FIGS. 4, (a) and (c). FIG. 4, (b) shows a result of sintering at 1350° C. It shows much more rough surface and porous structure as compared to when the sintering was performed at 1500° C. [(FIG. 4, (d)). In FIG. 4, (d), there are much fewer defects and pores caused by contraction and cracking as compared to FIG. 4, (c).

Also, the mechanical property of the biocompatible material may be changed through HAp resynthesis, particle growth, t-$ZrO_2$ synthesis, or the like. FIGS. 4, (e), (f) and (g) show an EDS analysis result of the composite of FIG. 4, (c) in (P, Q, R). The three layers are seen distinctly with no interlayer mixing during the extrusion processes.

Figure 5:
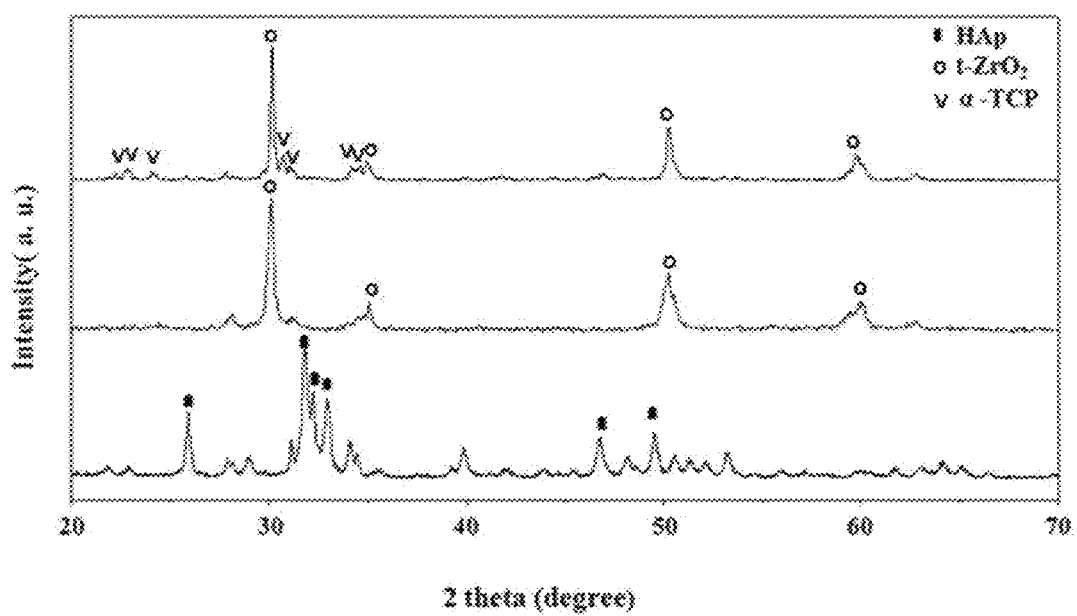
FIG. 5 shows XRD patterns of a TCP/TCP-(t-$ZrO_2$)/t-$ZrO_2$ composite before and after sintering.

FIG. 5 shows XRD patterns of the TCP/TCP-(t-$ZrO_2$)/t-$ZrO_2$ composite before and after sintering. The HAp peak observed before the sintering disappears afterwards due to the phase change at temperature as high as 1500° C. and thus the TCP peak appears.

[Test Example 1] Toxicity Test of TCP/TCP-(t-$ZrO_2$)/t-$ZrO_2$ Composite

Toxicity test was performed for the TCP/TCP-(t-$ZrO_2$)/t-$ZrO_2$ composite. The toxicity test was performed by MTT assay. Specifically, MG-63 cells were incubated for 72 hours with an eluate of the composite (0%, 12.55%, 25%, 50%, 100%) and viability of the cells was evaluated.

Cell viability for the eluates was 100%, 99%, 98% and 97%. Thus, it can be seen that the TCP/TCP-(t-$ZrO_2$)/t-$ZrO_2$ composite exhibits good biocompatibility with no toxicity.

[Test Example 2] Binding Safety Test of TCP/TCP-(t-$ZrO_2$)/t-$ZrO_2$ Composite

MG-63 cells were cultured on the TCP/TCP-(t-$ZrO_2$)/t-$ZrO_2$ composite at 37° C. for 15 minutes, 30 minutes and 60 minutes. After the culturing, the state of the cells was compared by taking SEM images.

The test result confirms the binding safety of the composite to the cells.

[Test Example 3] Physical Property Test of TCP/TCP-(t-ZrO$_2$)/t-ZrO$_2$ Composite Depending on Sintering Temperature Change in mechanical property and morphology of the TCP/TCP-(t-ZrO$_2$)/t-ZrO$_2$ composite was compared when the sintering temperature was 1350° C. and 1500° C. The result is shown in Table 1.

TABLE 1

| Sintering temperature (° C.) | Pore size of Haversian canals (μm) | Pore size of Volkmann canals (μm) | External diameter (mm) | Compressive strength (MPa) | Relative density (%) |
|---|---|---|---|---|---|
| 1350 | 82.8 ± 1.1 | — | 10.7 ± 0.3 | 32 ± 6 | 74.2 ± 5 |
| 1500 | 86.1 ± 5 | 377 ± 7 | 10.3 ± 0.3 | 53 ± 10 | 77.5 ± 1.5 |

Table 1 shows compressive strength and relative density of the TCP/TCP-(t-ZrO$_2$)/t-ZrO$_2$ composite for different sintering temperatures. The pore size, external diameter, compressive strength and relative density may be changed by controlling the alignment of the filaments and shells during the final extrusion and the sintering temperature.

In particular, it is to be noted that the compressive strength is about 53 MPa when the sintering temperature was 1500° C. whereas it was about 32 MPa when the temperature was 1350° C. This reveals that a better strength is obtained when the sintering temperature is 1500° C. as compared to when it is 1350° C. The relative density is also increased by 3.2% at 1500° C.

To conclude, a porous TCP/TCP-(t-ZrO$_2$)/t-ZrO$_2$ composite for fabrication of an artificial bone was fabricated successfully via the multi-pass extrusion process according to the present disclosure. Pore size, external diameter, compressive strength and relative density, which are the morphological and mechanical properties that determine the microstructure and mechanical stability, were 86 μm, 10.3 mm, 53 MPa and 77.5%, respectively, when the sintering temperature was 1500° C. The test showed that the sintering temperature affects the mechanical properties of the porous TCP/TCP-(t-ZrO$_2$)/t-ZrO$_2$composite. Particularly, the improvement in compressive strength (from 32 MPa to 53 MPa) is noteworthy. The pores and microcracks abundantly found when the sintering temperature was 1350° C. decreased significantly when the sintering temperature was 1500° C. Also, the MTT assay for the composite showed good cell viability of at least 96%, revealing very stable cell viability and superior biocompatibility of the material. It also exhibited good results for cell adhesion and dispersibility. Thus, it can be seen that the composite may be suitable as artificial bone for implantation in the human body.

The present application contains subject matter related to Korean Patent Application No. 10-2010-0072191, filed in the Korean Intellectual Property Office on Jul. 27, 2010, the entire contents of which is incorporated herein by reference.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

INDUSTRIAL APPLICABILITY

The method for fabricating an artificial bone according to the present disclosure allows fabrication of an artificial bone having the biocompatibility and mechanical strength of the natural bone and may be utilized variously in biomedical engineering, medicine and other applications.

The invention claimed is:

1. A method for fabricating an artificial bone by multi-pass extrusion, comprising:
    preparing a calcium phosphate shell, a calcium phosphate-(t-ZrO2) shell, and a t-ZrO2 shell by a warm pressing process;
    extruding the calcium phosphate/calcium phosphate-(t-ZrO2)/t-ZrO2 shells forming roll-shaped filaments as first extruded filaments, wherein each shell of the first extruded filaments is arranged in the order of calcium phosphate, calcium phosphate-(t-ZrO$_2$), and t-ZrO$_2$ from inside to outside;
    arranging the first extruded filaments circularly surrounding carbon filaments;
    extruding the roll-shaped and the carbon filaments as second extruded filaments;
    arranging an external shell of hydroxyapatite (HAp) surround the second extruded filaments and extruding the same as third extruded filaments, wherein the external shell of hydroxyapatite (HAp) is prepared by the warm pressing process;
    removing binder from the third extruded filaments by burning the third extruded filaments at 600-800° C.;
    removing carbon from the carbon filaments by burning the third extruded filaments at 900-1100° C.; and
    increasing a density of the third extruded filaments by sintering the third extruded filaments at 1350-1600° C.

2. The method according to claim 1, wherein the calcium phosphate is the hydroxyapatite (HAp).

3. The method according to claim 1, wherein, the carbon filaments are aligned at the center and comprised of carbon 48 vol %, ethylene vinyl acetate (EVA) 42 vol %, and stearic acid 10 vol %.

4. The method according to claim 1, wherein holes are formed in the third extruded filaments when the carbon is removed from the third extruded filaments.

5. The method according to claim 1, wherein the calcium phosphate is a tricalcium phosphate (TCP).

6. An artificial bone fabricated by the method according to claim 1.

* * * * *